US008178604B2

(12) United States Patent
Luchterhandt et al.

(10) Patent No.: US 8,178,604 B2
(45) Date of Patent: May 15, 2012

(54) SOLID MATERIALS OBTAINABLE BY RING-OPENING METATHESIS POLYMERIZATION

(75) Inventors: Thomas Luchterhandt, Greifenberg (DE); Peter Bissinger, Diessen (DE); Miriam Hansen, Munich (DE)

(73) Assignee: 3M Innovative Properties Company, Saint Paul, MN (US)

( * ) Notice: Subject to any disclaimer, the term of this patent is extended or adjusted under 35 U.S.C. 154(b) by 596 days.

(21) Appl. No.: 12/162,429

(22) PCT Filed: Jan. 30, 2007

(86) PCT No.: PCT/US2007/002576
§ 371 (c)(1),
(2), (4) Date: Nov. 18, 2008

(87) PCT Pub. No.: WO2007/089801
PCT Pub. Date: Aug. 9, 2007

(65) Prior Publication Data
US 2009/0088494 A1 Apr. 2, 2009

(30) Foreign Application Priority Data
Feb. 2, 2006 (EP) .................................... 06002150

(51) Int. Cl.
*C08J 5/32* (2006.01)
(52) U.S. Cl. ........ 524/265; 524/101; 524/236; 524/366; 524/283
(58) Field of Classification Search ........... 524/265.101, 524/236, 366, 283; 526/171
See application file for complete search history.

(56) References Cited

U.S. PATENT DOCUMENTS

| | | | |
|---|---|---|---|
| 5,854,299 A * | 12/1998 | Muhlebach et al. ............ | 522/66 |
| 5,861,443 A | 1/1999 | Hafner et al. | |
| 5,973,085 A * | 10/1999 | Muhlebach et al. .......... | 526/171 |
| 6,001,909 A * | 12/1999 | Setiabudi ...................... | 524/265 |
| 6,075,068 A * | 6/2000 | Bissinger ...................... | 523/116 |
| 6,235,856 B1 | 5/2001 | Hafner et al. | |
| 6,277,935 B1 | 8/2001 | Hafner et al. | |
| 6,410,110 B1 | 6/2002 | Warner et al. | |
| 6,455,029 B1 | 9/2002 | Angeletakis et al. | |
| 6,525,125 B1 | 2/2003 | Giardello et al. | |
| 6,649,146 B2 | 11/2003 | Angeletakis et al. | |
| 6,719,834 B1 * | 4/2004 | Braun et al. ...................... | 106/35 |
| 6,844,409 B2 * | 1/2005 | Angeletakis et al. ......... | 526/279 |
| 7,001,590 B1 * | 2/2006 | Angeletakis .................... | 424/49 |
| 7,173,097 B2 * | 2/2007 | Angeletakis .................. | 526/171 |
| 7,683,148 B2 * | 3/2010 | Angeletakis .................. | 526/171 |
| 7,691,919 B2 * | 4/2010 | Smolak et al. ................. | 523/115 |
| 2002/0153096 A1 * | 10/2002 | Giardello et al. .............. | 156/334 |
| 2003/0212233 A1 * | 11/2003 | Angeletakis et al. ........... | 528/15 |
| 2003/0220512 A1 * | 11/2003 | Blechert ......................... | 556/13 |
| 2004/0225073 A1 * | 11/2004 | Angeletakis ................... | 525/342 |
| 2004/0254320 A1 * | 12/2004 | Angeletakis ................... | 526/279 |
| 2005/0015951 A1 * | 1/2005 | Strebe ............................. | 28/178 |
| 2005/0159510 A1 | 7/2005 | Smolak et al. | |
| 2006/0004158 A1 * | 1/2006 | Moszner et al. .............. | 526/171 |
| 2006/0241257 A1 * | 10/2006 | Angeletakis .................. | 526/171 |
| 2009/0088494 A1 | 4/2009 | Luchterhandt et al. | |
| 2010/0036015 A1 | 2/2010 | Luchterhandt et al. | |

FOREIGN PATENT DOCUMENTS

| | | |
|---|---|---|
| CA | 2051333 | 3/1992 |
| CA | 2297442 A1 | 8/2000 |
| DE | 4029230 | 9/1990 |
| DE | 10 335 417 A | 2/2005 |
| EP | 771830 | 5/1997 |
| EP | 1317914 | 6/2000 |
| EP | 1025830 A2 | 8/2000 |
| EP | 1614410 | 1/2006 |
| EP | 1614410 A1 * | 1/2006 |
| EP | 1656924 | 5/2006 |
| JP | 63-128063 | 5/1988 |
| JP | 63-128065 | 5/1988 |
| JP | 17-200652 | 7/2005 |
| WO | WO 95/07310 | 3/1995 |
| WO | WO 9507310 A1 * | 3/1995 |
| WO | WO 96/16008 A1 | 5/1996 |
| WO | WO 96/16103 | 5/1996 |
| WO | WO 97/32913 A1 | 9/1997 |
| WO | WO 00/46257 | 8/2000 |
| WO | WO 02/14376 A | 2/2002 |
| WO | WO 03/093351 A1 | 11/2003 |
| WO | WO 2004/035596 A | 4/2004 |
| WO | WO 2004/101685 | 11/2004 |
| WO | WO 2005/053843 A | 6/2005 |

OTHER PUBLICATIONS

Mechanical Properties of a a Compositie Inlay Material Following Post-Curing, J.F. McCabe, S. Kagi, British Dental Journal, 1991: 171: 246.*
Castarlenas, R et al., *Journal of Organometallic Chemistr*, 663 (2002) 235-238.
Dexter et al., in *Encyclopedia of Polymer Science and Technology*, "Acoustic Properties to Cyclopentadiene and Dicyclopentadiene", Copyright © 2002, by John Wiley & Sons, Inc.; vol. 5, 164-183.
Hafner, A. et al (CIBA SC) *Angew. Chem. Int.*, "One-Component Catalysts for Thermal and Photoinduced Ring Opening Matathesis Polymerization", Ed. 36 (1997) 2121-2124.
Matos et al., *Journal of Molecular Catalysis A: Chemical 222*, "Piperidine as ancillary ligand in the novel [RuCl$_2$(PPh$_3$)$_2$(piperidine)] complex for metathesis polymerization of norbornene and norbornadiene", (2004) 81-85.
Slugovc et al., "Ring opening metathesis polymerisation in donor solvents", ChemCommun 2002, 2572-2573.

(Continued)

*Primary Examiner* — James J Seidleck
*Assistant Examiner* — Peter A Salamon
(74) *Attorney, Agent, or Firm* — Pamela L. Stewart

(57) ABSTRACT

The invention describes solid materials, especially for dental purposes like, e.g., composite milling blocks (CMBs), which can be obtained by ring-opening metathesis polymerization (ROMP). Also described is a method for obtaining such milling blocks, their use and applications of the compositions.

19 Claims, No Drawings

OTHER PUBLICATIONS

Vygodskii et al., *Macromolecules*, Ring-Opening Metathesis Polymerization (ROMP) in Ionic Liquids: Scope and Limitations, 2006, 39, 7821-7830.

XP-002434083, Weskamp et al., "Hochaktive Rutheniumkatalysatoren für die Olenfinmetathese: die Synergie N-hererocyclischer Carbene und koordinativ labiler Lindanden", Agnew: Chem 1999, vol. 111, Nr. 16, 2573-2576.

Search and Examination of EP Application No. 06002150; 7 pgs.
ISO/ISA for PCT/US2007/002576; 13 pgs.
Search and Examination of EP Application No. 06026426, 8 pgs.
ISO/ISA for PCT/US2007/087841; 15 pgs.
Andres Baltzer and Vanik Kaufmann-Jinoian, *Quintessenz Zahntechnik*, 30, 7, 726-740 (2004).

* cited by examiner

SOLID MATERIALS OBTAINABLE BY RING-OPENING METATHESIS POLYMERIZATION

CROSS REFERENCE TO RELATED APPLICATIONS

This application is a national stage filing under 35 U.S.C. 371 of PCT/US2007/002576, filed Jan. 30, 2007, which claims priority to European Application No. 06002150.8, filed Feb. 2, 2006, the disclosure of which is incorporated by reference in its entirety herein.

The invention describes precured compositions, especially for dental purposes like, e.g., composite milling blocks (CMBs), which are obtained by ring-opening metathesis polymerization (ROMP). Also described is a method for obtaining such milling blocks.

CMBs are polygonal, in many cases cylindric or cuboid molded specimen. They are pre-pared by filling pasteous curable formulations into a mold and subsequent curing of the pasteous material to give specimen of sufficient mechanical strength for milling or grinding. The cured specimen can optionally be cut to the desired shape and are often fixed on a sample holder for use in milling machines. Radical curing of such materials is often accompanied with undesirable high shrinkage of the specimen. As a result, those materials have high internal stress, which is often relieved by cracking of the specimen or by fraction or chipping during milling or during the usage in the oral cavity.

Recently, the introduction of ring-opening metathesis polymerisation (ROMP) has led to novel dental compositions which are characterised by a rapid polymerisation process, leading to partially or fully cured materials which display little volume shrinkage, little abrasion tendency and good mechanical properties.

U.S. Pat. No. 6,075,068 describes dental compositions containing polymerizable monomers and/or polymers, fillers, at least one initiator or one initiator system and usual auxiliaries including pigments, radio opaque additives and/or thixotropy aides. The polymerizable monomers and/or polymers have a chemical structure such that partial or final curing of the dental composition can be affected by ring-opening metathesis polymerisation (ROMP). The compositions contains mostly carbene-type initiators and are cured by the use of light.

U.S. Pat. No. 6,844,409 B2 relates to a composition curable by ring-opening metathesis polymerization and comprising an olefin-containing resin system and metathesis catalysts.

CA 2,297,442 A1 relates to compositions containing at least one bicyclic ring-system with 6 to 17 carbon atoms and at least one initiator for the ring-opening metathesis polymerization, wherein the by cyclic ring-system is not substituted by methacrylate groups. The systems cure at room temperature.

U.S. Pat. No. 6,001,909 relates to a composition used as encapsulating material for electrical or electronic components comprising a tight cycloolefin, a ROMP catalyst, a filler and a silane.

Composite milling blocks (CMBs) are widely used in prosthetic dentistry. Todays milling blocks in terms of curing chemistry are based on methacrylate technology (MAT). That means the polymerizable resins used in the pasteous formulations comprise esters of acrylic and/or methacrylic acid. CMBs are obtained by curing such formulations radically either by photoactivated generation of radicals or by thermal or redox generation of radicals. CMBs are often used for the production of e.g. crowns, inlays, onlays or partial crowns. To obtain these, CMBs are milled in computer controlled milling machines.

For dental applications aesthetics are crucial. Specimen produced by ROMP are usually heavily discoloured by the metal initiator present. Reducing the amount of initiator is limited with regard to polymerization speed and completeness. Thus, the color of CMBs pre-pared by ROMP remains a problem, as can be seen from U.S. Pat. No. 6,001,909, where in Example 1 samples received are described as "brownish grey" at a Ruthenium content of approximately 360 ppm.

There has been a need for CMBs prepared by ROMP which exhibit a colour fulfilling the requirements in a majority of dental applications of such CMBs. Surprisingly it has now been found, that prolonged exposure of specimen to elevated temperatures as they are applied during cure leads to a substantial discoloration of specimen making them applicable for dental restorations.

SUMMARY OF THE INVENTION

In a first aspect, the invention relates to a solid material, especially a dental material, obtainable by curing a composition comprising
a) at least one monomer that is curable by ring-opening metathesis polymerization (ROMP) with at least 1 functionality curable by ROMP,
b) at least one initiator for initiating the ROMP curing reaction and
c) at least one filler
wherein the cured composition is tempered at a temperature of more than about 130° C.

Another aspect of the invention relates to a process for the preparation of a solid material, especially a dental material, wherein a composition comprising
a) at least one monomer that is curable by ring-opening metathesis polymerization (ROMP) with at least 1 functionality curable by ROMP,
b) at least one initiator for initiating the ROMP curing reaction and
c) at least one filler
is cured and the cured composition is tempered at a temperature of more than about 130° C.

The invention further relates to the use of a cured composition according to the invention or of a cured composition prepared according to the invention as a material in dental applications, especially as an inlay, an onlay, a veneer shell, a crown or a bridge, either permanent or temporary, artificial teeth or denture bases or dentures.

A further aspect of the invention relates to an inlay, onlay, veneershell, crown or bridge, which comprises a cured composition according to the invention or a cured composition prepared according to the invention.

A further aspect of the invention relates to a method for the restoration of a tooth, comprising the step of milling a solid material according to the invention or a solid material prepared according to the invention. This can be done e.g. on a CEREC™ milling machine (Sirona Dental Systems) or a LAVA™ milling machine (3M ESPE AG) or any other computer aided device for milling or shaping prosthetic dental devices.

The solid material according to the invention can be used in any technological field where lightweight durable solid materials are needed. It is, however, preferably used as a dental material in the field of prosthetic dentistry and dental aesthetics. The solid materials according to the invention are preferably used in the form of blocks ready for milling, the so-called composite milling blocks (CMBs). Such blocks can be provided as such but can also be provided together with a mechanical holder, e.g. a holder especially adapted for certain milling machines.

The composite milling blocks according to the invention are cured by ROMP. Major advantages of ROMP-CMBs compared to prior art milling blocks cured by methacrylate polymerization can be very low shrinkage and shrinkage stress combined with superior mechanical properties, as high flexural strengths and fracture toughness. The ROMP-CMBs according to the invention can replace existing CMBs in dentistry and can broaden applicability of such devices due to their often superior properties. Broader applications can relate to access to broader variety of milling machines and new dental indications like provisional (short or long term) or permanent prosthetic restoration, especially bridges or dentures.

The solid ROMP-CMBs can also be produced in arbitrary shapes and used as they are or machined in other industries especially where high level mechanical properties and light weight application is desired like aeronautical or astronautical application.

In a solid material according to the invention, the composition to be cured comprises
a) about 9.999 to about 80% of at least one monomer that is curable by ring-opening metathesis polymerization (ROMP) with at least two functionalities curable by ROMP,
b) about 10 to about 5000 weight ppm of at least one initiator for initiating the ROMP curing reaction, the ppm value relating to the amount of metal in the initiator in relation to the amount of monomer and
c) about 19.999 to about 90% by weight of a filler or a mixture of two or more of such fillers.

The compounds mentioned above can be present in composition to be cured in an overall amount of 100% by weight, i.e., the amount of substances chosen from a substance as described under a) above, as described under b) above and described under c) above can add up to 100% by weight. It is, however, also possible that a composition to be cured comprises one or more adjuvants besides the substances chosen from a substance as described under a) above, as described under b) above and described under c). In this case, the above amounts can add up to less than 100% by weight.

The fillers can be treated with interfacial compounds that chemically link to the surface of fillers used and are able to incorporate into the polymer network produced by ROMP. Further additives can be modifiers, opacity modifiers, softeners, solvents, compatibilizer, rheology modifiers, colour pigments, organic or inorganic fibres.

In a further aspect of the invention a process for the preparation of a solid material is described, wherein a composition comprising
a) at least one monomer that is curable by ring-opening metathesis polymerization (ROMP) with at least one functionality curable by ROMP,
b) at least one initiator for initiating the ROMP curing reaction and
c) at least one filler
is cured and the cured composition is tempered at a temperature of about 130° C. or more.

Tempering of a specimen of a cured composition for hours at temperatures as high as about 130° C. or about 160° C. or about 180° C. generally does not lower mechanical properties especially fracture toughness or Youngs' modulus. Sometimes these mechanical properties can even be improved.

Tempering of a specimen of a cured composition for hours at temperatures as high as about 130° C. or about 160° C. or about 180° C. on the other hand can lead to increased lucency of the specimen. Unfavourable discoloration coming from the initiator present in the specimen often surprisingly can be reduced by this thermal process. Quantitatively this can be monitored by means of color analysis e.g. according to the L*a*b scheme (CIELAB system: L*: Lightness; a*: values on the red/green axis; b*: values on the yellow/blue axis). Tempering leads to a higher L*-value (closer to 100), meaning the increasing lightness, and an a* value closer to about 0 or a b*-value closer to about 0.

Decoloration often can be noted to be favourably influenced by the exclusion of oxygen. If samples are exposed to oxygen during tempering at the surface, one or more colored stains can sometimes be observed, while the bulk of material shows the desired decoloration. The surface stains can, however, be removed by polishing. Under a nitrogen atmosphere decoloration is generally observed both in the bulk material and on the surface of the tempered specimen.

The invention also relates to the use of a cured and tempered composition according to the invention as a material in dental applications. Dental applications can be prosthetic provisions especially inlays, onlays, veneer shells, crowns or bridges, either temporary or permanent.

The solid material according to the invention is preferably provided in the form of a composite milling block (CMB), comprising a solid material according to the invention or a solid material prepared according to a process of the invention and a mechanical holder fit for a milling machine.

The invention also relates to a method for the restoration of one or more teeth of a mammal, especially of a human being, comprising the step of milling a dental material according to the invention or a dental material prepared according to the invention.

DETAILED DESCRIPTION OF THE INVENTION

A solid material according to the invention is obtained by subjecting a composition comprising at least one monomer that is curable by ring-opening metathesis polymerization (ROMP) with at least one functionality curable by ROMP such as at least 1 endocyclic olefinically unsaturated double-bond, at least one initiator for initiating the ROMP curing reaction and at least one filler to ROMP. However; it has often proven to give good results, if at least a fraction of the monomers in the composition, which is often also called a polymerizable matrix composition, have two or more functionalities curable by ROMP, e.g., two or more endocyclic olefinically unsaturated doublebonds which are curable by ROMP.

The curable polymerizable matrix composition preferably comprises at least one monomer that has two or more moieties polymerizable by ROMP with a fraction of at least about 1% by weight. The amount of monomer that has two or more moieties polymerizable by ROMP can be higher, e.g., at least about 10, about 20, about 30, about 40, about 50 or about 60% by weight of the monomers in the composition or even higher, e.g., more than about 70, more than about 80, or even about 90% by weight.

Generally, all types of monomers can be part of the composition which have one moiety or preferably two or more moieties that can be polymerized by ROMP.

Generally, suitable monomers can follow the general formula $B-A_n$ wherein A is a moiety polymerizable by ROMP preferably cyclobutenyl, cyclopentenyl, cyclooctenyl or bicyclic ring systems like the often preferred norbornenyl and 7-oxa-norbornenyl groups, B is an organic or silicon-organic backbone with 1 to about 100, e.g., 1 to about 10 or 1 to about 5 or 1 to about 4 moieties polymerizable by ROMP, e.g., 2 or 3 moieties polymerizable by ROMP, are attached, n being about 1 to about 100. The composition according to the invention can contain only one type of monomers according to the general formula B-A$_n$. It is also possible that a composition according to the invention contains two or more different types of monomers according to the general formula B-A$_n$. The composition according to the invention preferably contains at least one type of monomer according to the general formula B-A$_n$, which has one or preferably two olefinically unsaturated double bonds which are curable by ROMP.

The bicyclic ring systems which can be used according to the invention preferably have no exocyclic C—C double bonds like (meth)acrylate groups so that the curing of the compositions takes place at least predominantly by ring-opening metathesis polymerization (ROMP). Furthermore, it can in some instances be advantageous if the bicyclic ring systems also contains no vinyl or allyl groups as these sometimes may function as a chain-terminating agent during ROMP. Despite that, however, addition of chain terminating agents in order to regulate polymerization can be preferred.

The compositions according to the invention can contain bicyclic ring systems with 1 to 2 endocyclic double bonds. Carbocyclic ring systems are particularly preferred as well as oxygen-substituted ring systems.

Carbocyclic and heterocyclic bicyclo[x.y.z.] hydrocarbons with noticeable ring strain may often be particularly suitable, when x, y and z have values from 1 to 6. x is equal to about 2, y is equal to about 2 and z equal to 1.

Preferred representatives of this composition class are derivatives of bicyclo[2.2.1]heptene or 7-Oxa-bicyclo[2.2.1] heptene in particular those with unsaturation in 5-position and substitution in 2- or 2,3-position to the ring. Substituents in 2- or 2,3-position to the ring are preferably carbon-silicon- or oxygen-functional and connect to an unreactive residue or to an organic or metalorganic spacer bridging between two, three, four or more ROM-polymerizable groups.

Preferred representatives of this composition class are bicyclo[2.2.1]heptene derivatives and 7-Oxa-bicyclo[2.2.1] heptene derivatives, in particular those according to the following formulae,

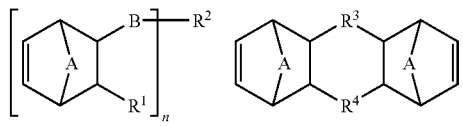

in which n, A, B, R$^1$, R$^2$, R$^3$ and R$^4$, independently from each other, have the following meanings:
A=—CH$_2$— or —O—;
R$^1$=—H; C$_1$ to C$_{12}$ alkyl, aryl or benzyl, preferably C$_1$ to C$_{12}$ alkyl, phenyl or benzyl, in particular methyl, ethyl, propyl butyl, hexyl, octyl, decyl, dodecyl, phenyl, benzyl; —C(=O)—OR$^5$; —O—C(=O)—R$^5$; —CH$_2$—O—C(=O)—R$^5$; R$^5$ standing for —H, C$_1$ to C$_{12}$ alkyl, aryl or benzyl, preferably C$_1$ to C$_{12}$ alkyl, phenyl or benzyl, in particular methyl, ethyl, propyl butyl, hexyl, octyl, decyl, dodecyl, phenyl, benzyl;
B=—O—, —CH$_2$—, —CH$_2$—O—, —CH$_2$—O—(CH$_2$—CH$_2$—O)$_m$— (with m=1, 2, 3, 4 or 5), —C(=O)—, —C(=O)—O— or is absent;
n=an integer from 1 to 6, preferably 1 to 4, especially 1 to 3;
R$^2$=n-times substituted organic or metalorganic residue C$_1$ to C$_{24}$ that can contain O, N and Si atoms, preferably C$_1$ to C$_{12}$ alkylene, C$_6$ to C$_{24}$ arylene, preferably bisphenol type backbones, biphenylenes, phenylene or naphthylene, discrete siloxanes or carbosilanes;
R$^3$, R$^4$=C$_1$ to C$_{20}$ alkylene, preferably C$_1$ to C$_{12}$ alkylene, in particular C$_1$ to C$_3$ alkylene; a chemical bond, —O— or R$^4$ and R$^4'$ together form a >CH—CH$_2$—CH< radical;
as well as stereoisomeric compounds and any mixtures of these substances.

The radicals B, R$^1$, R$^2$, R$^3$ and R$^4$ can be bound in the endo- or exo position. Typically the bicyclic compounds according to the above formulae are present in the form of stereoisomeric mixtures, in particular as racemates.

Preferred compounds are often accordingly those in which at least one of the variables of the formulae has a preferred definition as described above. Also preferred can be those compounds in which several or all of the variables correspond to the preferred definitions.

Quite particularly preferred bicylic ring systems are bicyclo[2.2.1]hept-2-en (norbornene), 7-oxa-bicyclo[2.2.1]hept-2-ene (7-oxa-norbornene) and substituted derivatives derived therefrom such as esters of bicyclo[2.2.1]hept-5-en-2-carboxylic acid or esters of bicyclo[2.2.1]hept-5-en-2,3-dicarboxylic acid, both with mono-, di- or multifunctional alcohols, esters of bicyclo[2.2.1]hept-5-en-2-ol or bicyclo[2.2.1] hept-5-en-2-methanol or bicyclo[2.2.1]hept-5-en-2-(methoxy-(2-hydroxy)ethan with mono-, di- and multi carboxylic acids or the reaction products of the mentioned bicyclic alcohols with mono- or diisocyanates.

The corresponding structural formulae are given below for suitable bicyclic ring systems, the formulae also representing the corresponding position isomers which result from the exchange of substituents R$^1$, R$^2$ and R$^3$, with —R—=—(CH$_2$)$_n$—, n is equal to 1 to 4 and the ring containing O and R is in the endo- or exo position relative to the norbornene system.

Preferred monomers, which can be used are given in the lists below:

MONOMERLIST 1

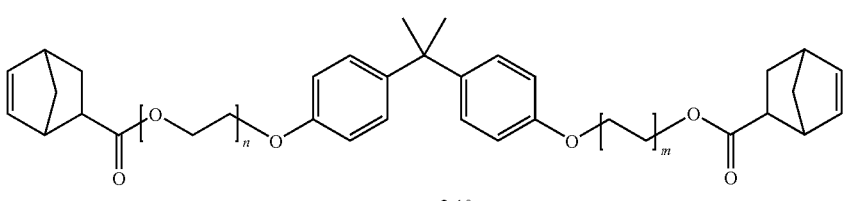

n + m = 2-10

-continued
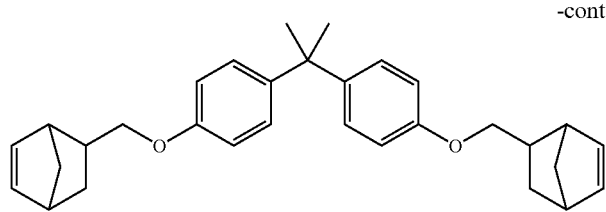
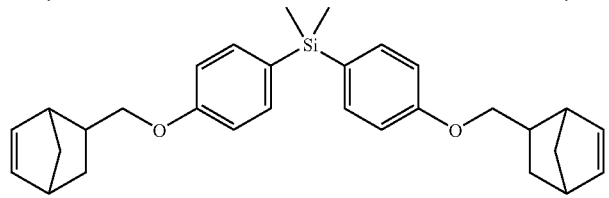
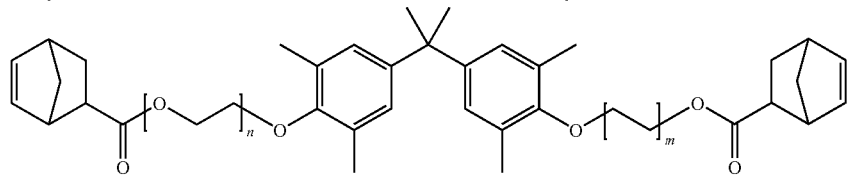
n + m = 2-10
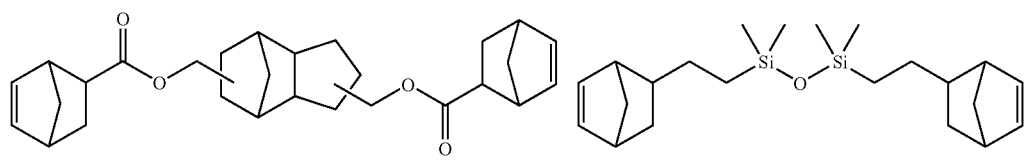
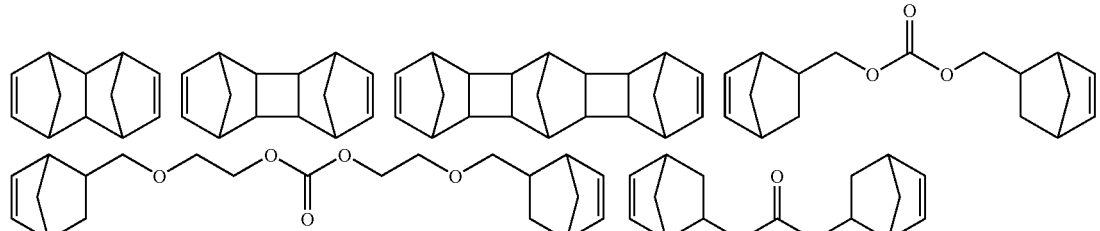
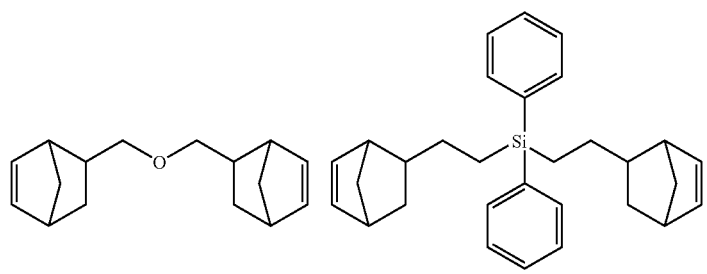
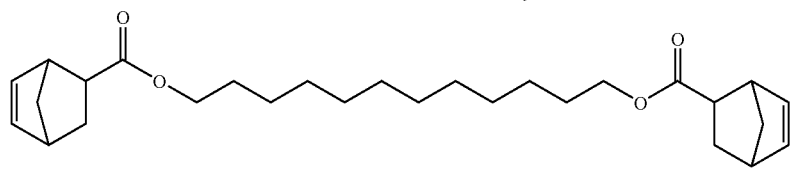
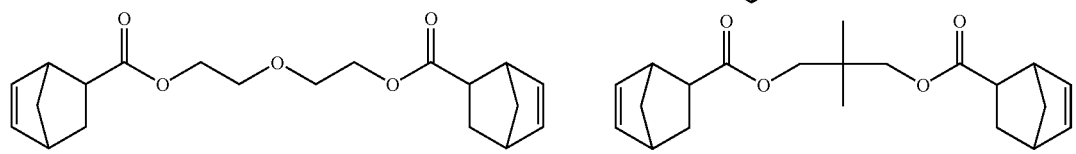
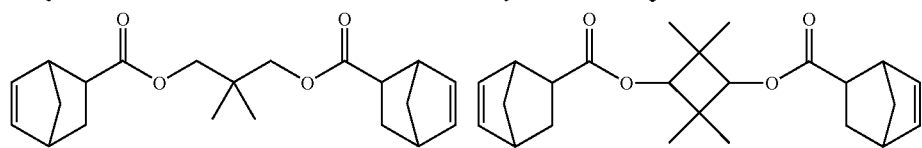

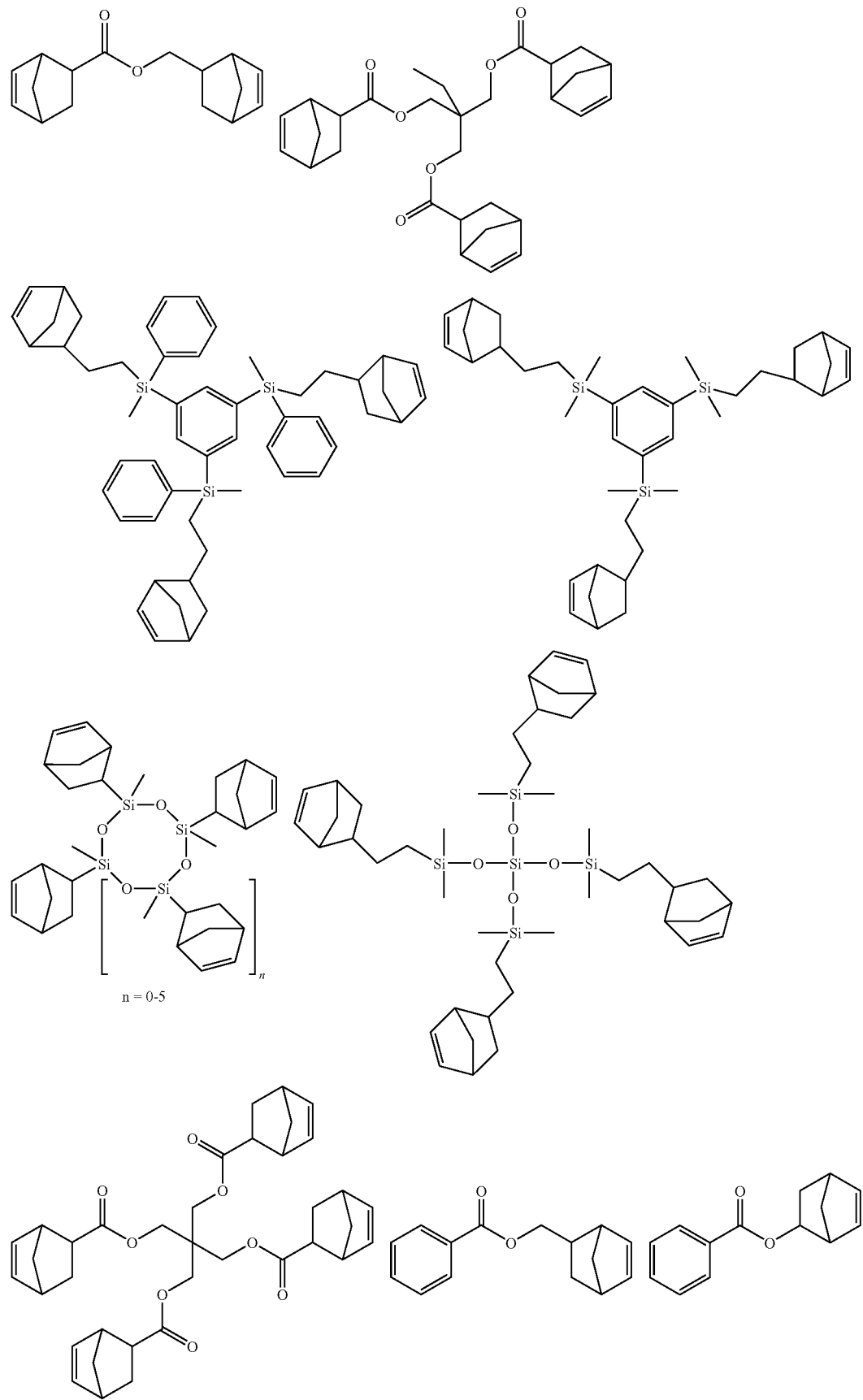

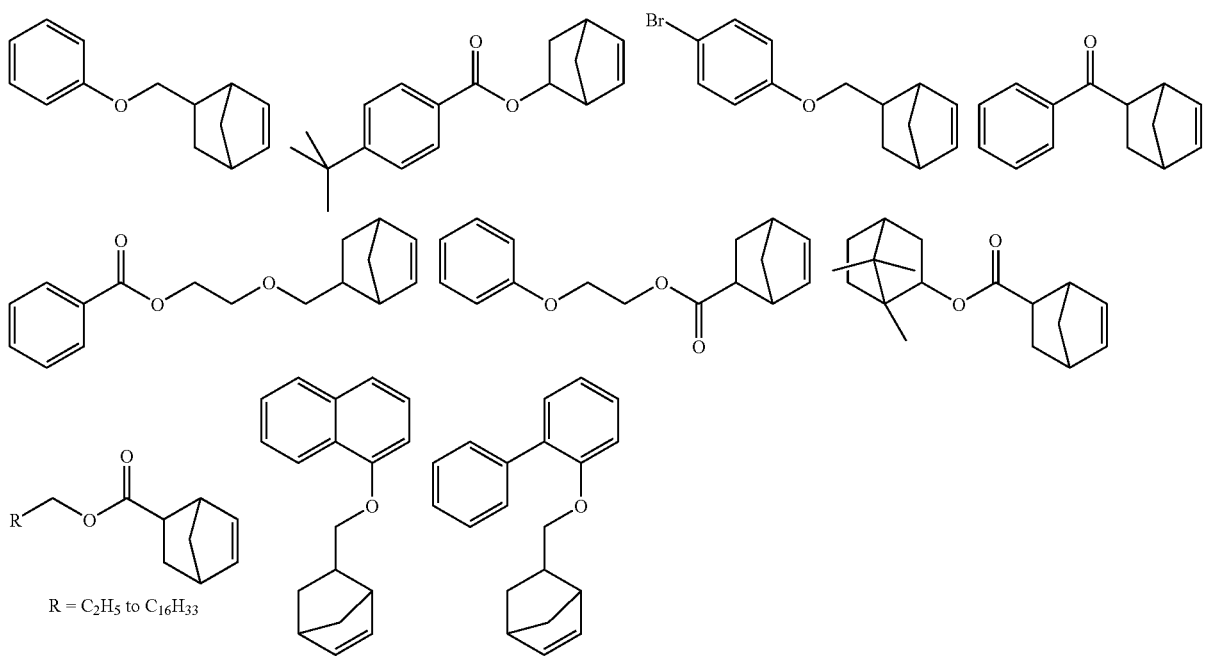

With any norbornene (bicyclo[2.2.1]hept-5-enyl) group in the preceding formulas the corresponding 7-oxa-norbornene (7-oxa-bicyclo[2.2.1]hept-5-enyl) derivatives are comprised as well. For reason of simplicity stereoisomers at the norbornene moiety are generally not explicitly mentioned in the formulae. It should, however, be understood that all isomers either exo- or endo- to the norbornene ring and mixtures of both are comprised. The two-dimensional formula

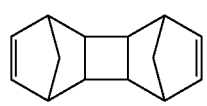

therefore refers to any of the following isomers or possible others and mixtures of all of these:

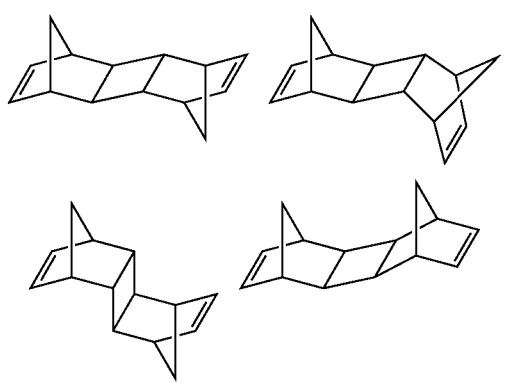

Accordingly, showing one enantiomeric Norbornenyl-Isomer in any case means also the other enantiomer or a mixture of those:

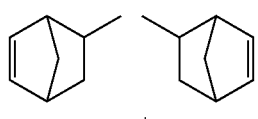

two enantiomers

The bicyclic ring systems listed are easily accessible through the known cyclisation reactions such as e.g. cyclo additions, especially Diels-Alder reactions. They are generally stable and not moisture-sensitive at room temperature and in the presence of conventional dental fillers.

In another embodiment of the invention, the polymerizable matrix composition comprises one or more oligomeric or prepolymeric structures e.g. polyether, polyester or polysiloxane or copolymeric compounds (PDMS) that are tethered and/or end-capped with groups that can undergo a ROMP reaction to form a cured article.

Other preferred oligomeric and polymeric monomers are described in the list below

MONOMERLIST 2:

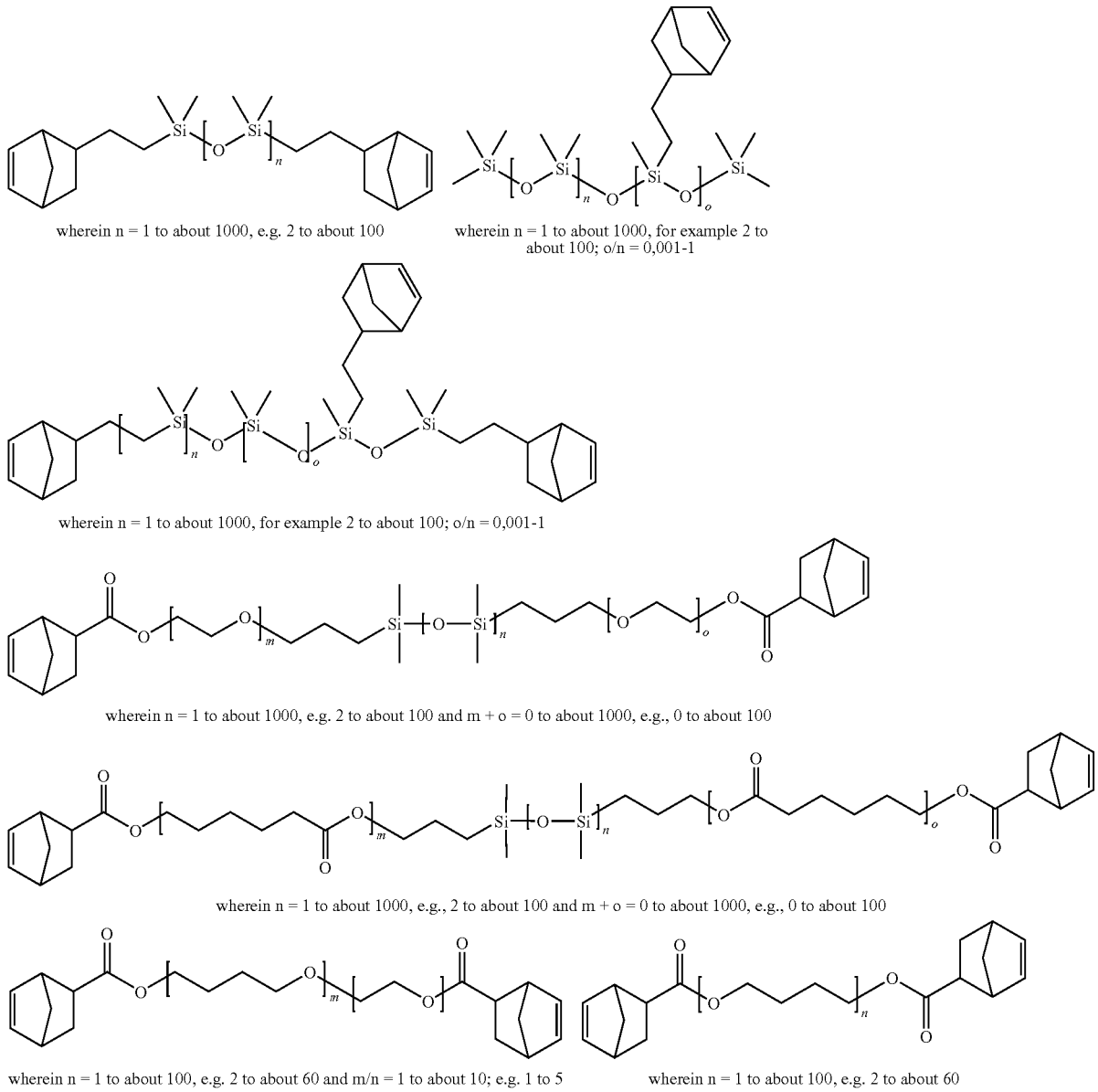

Yet another category of oligomers and/or polymers that may be used in compositions of the invention include tri- or quadrifunctional oligomers or polymers having siloxane backbone end-functionalized or end-capped with an olefin group curable by a metathesis reaction, such as cycloalkenyl groups, for example norbornenyl or norbornenylethyl groups. An example of such polymer is quadrifunctional polydimethyl siloxane (PDMS), end-capped with norbornenyl (NBE) groups.

In addition to the above categories of oligomers and polymers, the resin system may comprise any other polymerizable cycloalkenyl-functionalized siloxane based oligomers or polymers that may undergo polymerization via ROMP mechanism.

Monomers taken from MONOMERLIST 1 may provide particularly beneficial results.

It can also be advantageous if contains at least one monomer with two moieties polymerizable by ROMP and a molecular weight of more than about 180, especially more than about 200 or more than about 250 or more than about 300. The upper limit for the molecular weight should be in a range where the handling of the composition with regard to its formability is still possible (the composition is not a solid and too viscous to be formed) and the material properties of the cured composition are in a desired range.

The amount of monomer (component a)) that is curable by ring-opening metathesis polymerization (ROMP), can often vary between about 10 and about 90% by weight. In many cases an amount of about 15 to about 50 or about 20 to about 40% by weight, can lead to good results.

The composition to be cured also contains an initiator (component b)) or a mixture of two or more initiators. Suitable initiators are generally all substances which are able to initiate a ROMP polymerization in a curable composition according to the invention. It is preferred if a curable composition comprising an initiator is sufficiently chemically stable at ambient temperature, generally at room temperature or temperatures up to about 60° C., providing unhindered preparation and molding of the formulation.

Suitable chemically stable initiators do not lead to an increase of viscosity of the composition of more than about 10% during a minimum of about 5 hours at temperatures below about 50° C. It is also preferred if a suitable initiator will cure the formulation within about 24 hours at a temperature above about 100° C. by ROMP reaction. Preferred initiators are metal complexes of ruthenium or osmium not bearing a carbene function. Examples of suitable initiators can be found in Castarlenas et al., *Journal of Organometallic Chemistr,* 663 (2002) 235-238 and in Hafner et al., *Angew. Chem.* 1997, 109, Nr. 19, S. 2213. These references and especially their disclosure with regard to initiators for ROMP are expressly mentioned herein and the disclosure is considered as being part of the disclosure of the present text.

Further preferred initiators are disclosed in U.S. Pat. No. 6,001,909 col. 10 1.51 to col. 13, 1.14 and col. 13, 1.66 to col. 15, 1.65. This references and especially its disclosure with regard to non photolabile initiators for ROMP are expressly mentioned herein and the disclosure is considered as being part of the disclosure of the present text.

Preferred initiators follow the formula

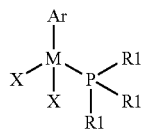

where
M=Ru or Os
Ar=aromatic ligand like benzene, toluene, xylene, cymene, anisole
X=an anionic ligand like halogenide (F, Cl, Br, I), alkoxy, trifluormethansulfonate, trifluoracetate
R1=independently chosen an alkyl residue $C_3$-$C_{12}$ preferably a secondary or tertiary alkyl residue like isopropyl, cyclohexyl, cyclopentyl, cyclopropyl, tert.-butyl
Especially suitable initiators are

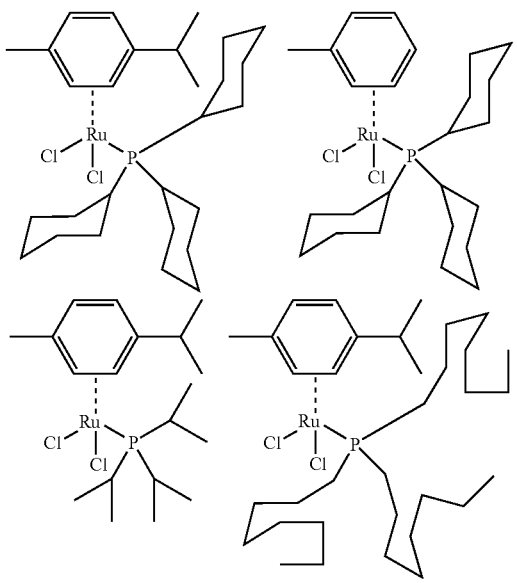

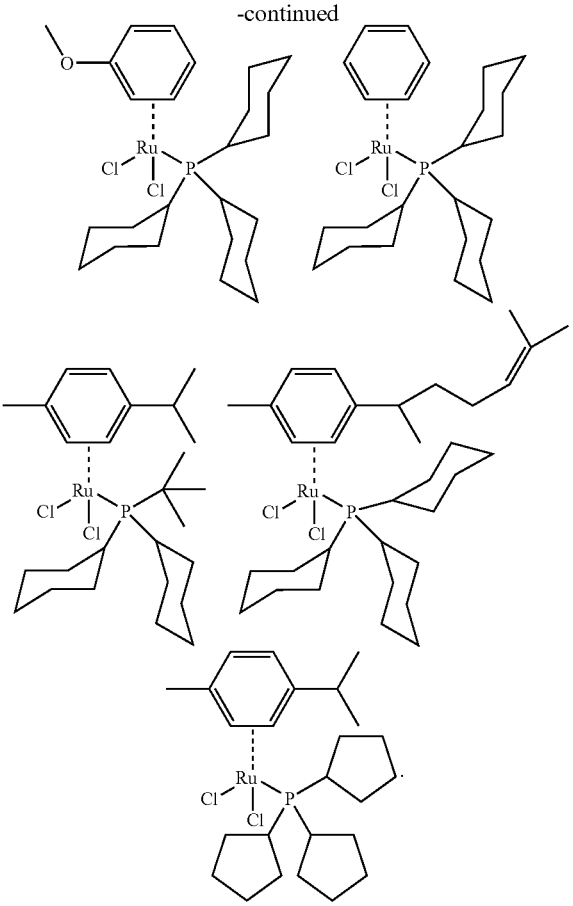

The amount of initiator should be chosen such that the composition cures at temperatures above about 100° C. within a time frame of about 24 h by ROMP. Sufficient amounts of initiator are, e.g., about 5 ppm to about 10000 or about 10 ppm to about 5000 ppm or about 20 ppm to about 2000 ppm, the ppm being weight ppm Ruthenium in relation to the amount of the composition to be cured.

The composition to be cured also contains a filler or a mixture of two or more fillers (component c)), e.g., organic or inorganic fillers, preferably inorganic fillers). Fillers can be solid materials, e.g., ground inorganic materials like all modifications of $SiO_2$ (e.g. quartz, christobalite) or glasses or precipitated material or material obtained by sol-gel procedures like "chemical ceramics" or organic or inorganic fibres, felts or beads as well as highly dispersed fumed or precipitated fillers ($SiO_2$, $ZrO_2$ or other metal oxides) or nanoshaped spherical or clustered metal oxides which preferably can enhance the mechanical properties of the cured composition. The size of used filler often ranges (but is not limited to) from several microns, down to a few nm.

Preferred particulate fillers can be amorphous materials on the basis of mixed oxides comprising $SiO_2$, $ZrO_2$ and/or $TiO_2$ as are described for example in DE 40 29 230 A1, micro-fine fillers such as pyrogenic silicic acid or precipitation silicic acid as well a macro- or minifillers such as quartz, glass ceramic or glass powders with an average particle size of about 0.01 to about 5 μm as well as X-ray opaque fillers, such as ytterbium trifluoride. Furthermore glass fibres, polyamide or carbon fibres can be used as fillers.

Particularly preferred fillers are mixtures of (a) amorphous spherical particles comprising silicon dioxide and up to about 20 mol-% of an oxide of at least one element of the groups I, II, III and IV of the periodic system with a refractive index of about 1.45 to about 1.58 and an average primary particle size of about 10 nm to about 10 μm and (b) quartz, glass ceramic or glass powders or their mixtures with a refractive index of about 1.45 to about 1.58 and an average particle size of about 0.5 to about 5 μm.

A composition to be cured according to the invention can contain only one type of fillers. It is also possible and preferred that a composition to be cured according to the invention contains two or more different types of fillers. Different types of fillers can differ in chemical constitution, shape, size, size distribution or other features or combinations of two or more of the above mentioned features.

The fillers can be modified by interfacial compounds. Interfacial compounds are sub-stances that chemically link to the surface of fillers, e.g., by condensation, and are able to incorporate into the polymer network produced by ROMP. Usually, they comprise two different functionalities. One functionality is able to chemically bond to the surface of the filler material, the second functionality is able to crosslink with the monomer matrix, normally through a ROMP reaction. Preferred substances are silanes described by the general formula $X_a R_b SiR^1_{(4-a-b)}$, wherein X is hydrogen, halogen, hydroxyl, alkoxy, acyloxy, alkylcarbonyl, alkoxycarbonyl or $-NR''_{12}$ preferably methoxy or ethoxy; R is alkyl, alkenyl, aryl, alkylaryl or arylalkyl; R'' is hydrogen, alkyl or aryl; $R^1$ is an organic group comprising an unsaturated strained cycloaliphatic group that is able to incorporate into a polymeric network obtained by ROMP, preferably norbornenyl, 7-oxa-norbornenyl, cyclobutenyl, cyclopentenyl or cyclooctenyl, a is 1, 2 or 3; b is 0, 1 or 2 and (a+b<4). Preferred examples are:

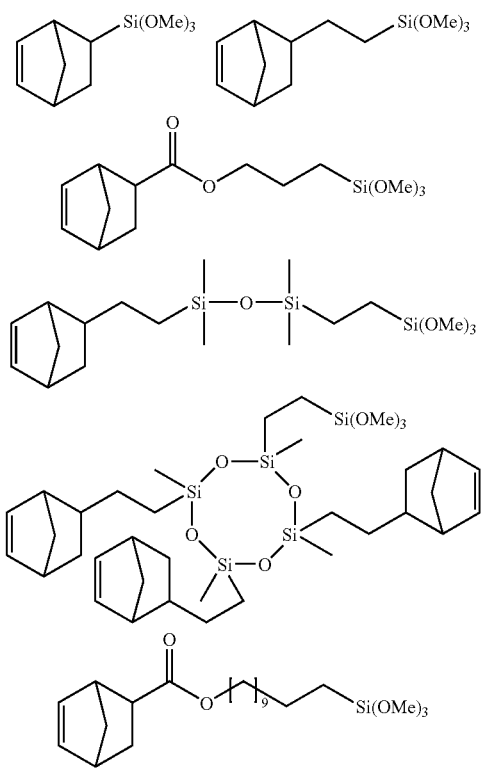

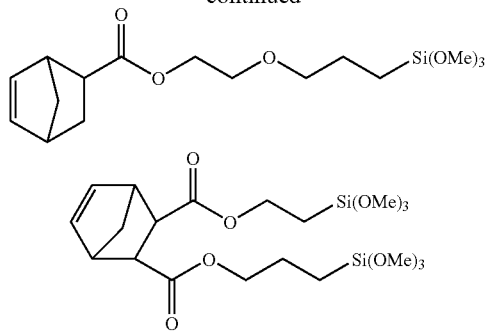

The compositions to be cured according to the invention contain fillers in an amount of about 10 to about 90% by weight, preferably in an amount of about 40 to about 85 or about 60 to about 80% by weight. It can be preferred if the filler contains different compounds, differing with regard to their size, e.g. structural fillers and microfillers. The amount of micro fillers can be 0 to about 50% by weight.

The composition to be cured preferably comprises
 a) about 9.999 to about 50% by weight of a monomer that is curable by ring-opening metathesis polymerization (ROMP) or a mixture of two or more of such monomers,
 b) about 100 to about 3000 weight ppm of at least one initiator for initiating the ROMP curing reaction, the ppm value relating to the amount of metal in the initiator in relation to the amount of monomer and
 c) about 49.999 to about 90% by weight of a filler or a mixture of two or more of such fillers.

In addition, the compositions can contain further auxiliaries if need be such as stabilizers, UV absorbers, dyes, pigments and/or slip agents. The auxiliaries are used optionally in an amount of up to approximately about 0.5 wt.-% each.

Suitable stabilizers are for example hydroquinone monomethyl ether or 2,6-di-tert.-butyl-4-methylphenol (BHT).

A composition to be cured according to the invention can further contain one or more modifiers that exhibit influence on stability of the uncured formulation or the curing process. Stabilizers can be substances that compete successfully but reversibly with phosphine ligands at the ruthenium coordination site, promoters can be substances that trap phosphine ligands and prevent them from recoordination like copper(I) ions or substances that convert ruthenium complexes to a more reactive one like agents that produce ruthenium carbene species like phenyl acetylene.

A composition to be cured according to the invention can further contain one or more opacity modifiers. As opacity modifiers substances can be used which have a high ability to scatter the light in the matrix, preferably substances which show sufficiently different refractive indices to the rest of the formulation e.g. $TiO_2$, $Al_2O_3$, $YF_3$ or $YbF_3$. A composition to be cured according to the invention can further contain additives like softeners, solvents, compatibilizer, rheology modifiers, colour pigments, organic or inorganic fibers.

The composition to be cured should be at least in a pasteous and formable or pourable liquid state. The viscosity of the composition should be above about 100 mPas and below about 10 Pas in order to be able to easily bring the composition into a desired shape prior to curing.

The Brookfield viscosity of the composition is preferably within a range of about 10 to about 100000 mPas or about 20 to about 50000 mPas.

The invention also relates to a process for the preparation of a solid material as described above, wherein a composition comprising at least one monomer that is curable by ring-opening metathesis polymerization (ROMP), at least one initiator for initiating the ROMP curing reaction and at least one filler is cured and the cured composition is tempered at a temperature of more than about 130° C.

A cured composition according to the invention can generally be cured and tempered in one single step. In this case, if the composition is cured in an appropriate heating device, it can be simply left in the heating device until curing and tempering are effected to the desired extent. If curing takes place at a temperature below the minimum tempering temperature of about 130° C., the temperature in the heating device can be adjusted accordingly to reach the desired level for curing.

In the process according to the invention curing and tempering can also be effected in separate steps. Thus, the composition to be cured can first be cured at an elevated temperature and then, e.g., cooled down and stored and in a successive step be tempered at a temperature of about 130° C. or more.

The curing and tempering can be effected at equal or different temperatures. It can be advantageous, if curing is performed at temperatures of less than about 130° C., e.g., at temperatures of more than about 50° C. to less than about 150° C., e.g., between about 80° C. and about 140° C. It is, however, also possible, to effect curing at the same temperature as tempering, e.g., at a temperature of more than about 130° C., e.g., about 160° C. or more, e.g., more than about 170° C. or more than about 180° C. The upper limit for the curing temperature is usually a temperature, where the material properties are disadvantageously affected by the curing process. It has often proven to be successful, if the curing temperature is below about 250° C.

The curing time can be chosen such that the desired improvements of one or more material properties are achieved. Generally, if the focus of improvement of properties lies in the physical properties of the material, the cured composition can, e.g., be tempered until the compressive strength or the flexural strength or the fracture toughness or the Youngs modulus or combinations of two or more of those features are improved over the untempered material.

If the focus of improvement of properties lies in the optical properties of the cured composition, the composition is at least tempered until the color of the tempered material according to the CIE L*a*b*-color scheme has an L-value closer to about 100 or an absolute a-value closer to about 0 or an absolute b-value closer to about 0 or a combination of two or more of these improvements, as compared to the untempered material.

CIE L*a*b* (CIELAB) is often regarded as being the most complete color model used conventionally to describe all the colors visible to the human eye. It was developed for this specific purpose by the International Commission on Illumination (Commission Internationale d'Eclairage, hence the CIE acronym in its name). The * after L, a and b are part of the full name, since they represent L*, a* and b*, derived from L, a and b.

The three parameters in the model represent the luminance of the color (L, the smallest L yields black), its position between red and green (a, the smallest a yields green) and its position between green and blue (b, the smallest b yields blue).

In a preferred embodiment a solid material according to invention fulfills at least one of the following parameters:

| | |
|---|---|
| Flexural strength: | at least about 155 MPa, |
| Youngs' modulus: | at least about 9200 MPa, |
| L-value: | more than 68, |
| a-value: | less than 4 and |
| b-value: | less than 20.5. |

The minimum tempering time can be as low as about 5 minutes. Generally, it has proven to be successful in many cases if the minimum curing time is about 10 to about 30 minutes. Good results can be achieved with many materials with a curing time of about 30 to about 300 minutes, e.g., about 90 minutes or more or between about 90 and about 180 minutes, e.g., about 100 to about 150 minutes.

Generally, the process according to the invention can be performed in any way suitable for achieving the desired result. It can be advantageous to first fill the composition to be cured into a form which has the desired shape and cure the composition at an elevated temperature. Tempering of the cured composition can be performed either in direct succession to curing of after cooling of the cured composition. The cured composition can be tempered while still in the curing form. It is also possible to first remove the cured composition from the form and then temper the cured composition.

The solid material according to the invention can generally be used in all technical fields where lightweight and durable ROMP materials are needed. According to a preferred embodiment of the invention, the solid material is used as a material in dental applications, e.g., as an inlay, an onlay, a veneer shell, a crown or a bridge, either temporary or permanent, artificial teeth or denture bases or dentures.

Dental applications as described above are often prepared by subjecting a precured material to a mechanical milling step, preferably by a CMC milling machine. Such machines often use special mechanical holders which are especially adapted for precisely holding the specimen to be milled in place. The invention thus also provides for a dental milling block (DMB), comprising a solid material according to the invention or a solid material prepared according to the invention and a mechanical holder fit for a milling machine.

The invention also relates to a method for the restoration of a tooth, comprising the step of milling a solid material according to the invention or a solid material prepared according to the invention.

The following examples illustrate the invention:

In the examples below, the ingredients for the inventive Examples are described. The listed ingredients are kneaded to a paste, test samples made according to the ISO test procedure and then tested. The results for flexural strength and Youngs modulus are given. Additionally the L*a*b* numbers are listed.

Example

Compound 1:

1. 6 g Monomer:

2. 0.017 g Initiator:

3. 15 g Filler:
   Quarts (Median: 0.7 μm)
   silanized with 6 wt.-%

Preparation of the paste: The monomer, initiator and filler were mixed into a paste with a Speed Mixer™ DAC 150 FVZ (Hauschild Engineering), the conditions used were 2200 rpm for 3 minutes, 3 times. The paste was allowed to cool to room temperature before each mixing time.

Flexural strengths and Youngs's modulus were tested according to ISO 4049:2000.

Determination of L*a*b-values were made with a Hunter-Lab Scan-2 (Hunterlab, Va., USA).

The results obtained after tempering the cured compounds are described in the following tables.

A specimen was regarded as having fulfilled the test for a certain parameter, if the following values were met or exceeded:

| Flexural strength: | >155 MPa |
|---|---|
| Youngs' Modulus: | >9200 |
| L-value: | >68 |
| a-value: | <4 |
| b-value: | <20.5. |

TABLE 1

| | Tempering time and temperature | | | | |
|---|---|---|---|---|---|
| | 2 h 130° C. | 4 h 130° C. | 8 h 130° C. | 16 h 130° C. | 24 h 130° C. |
| Flexural strength[MPa] | − | + | + | − | − |
| Youngs' Modulus [MPa] | − | + | + | − | − |
| L* | − | − | + | + | + |
| a* | − | − | + | + | + |
| b* | + | + | + | − | + |

TABLE 2

| | Tempering time and temperature | | | | |
|---|---|---|---|---|---|
| | 2 h 160° C. | 4 h 160° C. | 8 h 160° C. | 16 h 160° C. | 24 h 160° C. |
| Flexural strength [MPa] | − | − | + | − | − |
| Youngs' Modulus [MPa] | + | + | + | − | + |
| L* | + | + | + | + | + |
| a* | + | + | + | + | + |
| b* | + | + | + | + | + |

TABLE 3

| | Tempering time and temperature | | | |
|---|---|---|---|---|
| | 2 h 180° C. | 4 h 180° C. | 8 h 180° C. | 16 h 180° C. |
| Flexural strength[MPa] | − | + | − | − |
| Youngs' Modulus [MPa] | + | + | + | − |
| L* | + | + | + | + |
| a* | + | + | + | + |
| b* | + | + | + | + |

The invention claimed is:

1. A composite milling block (CMB), comprising a mechanical holder fit for a milling machine and a solid material obtained by curing a composition comprising
   a) at least one monomer that is curable by ring-opening metathesis polymerization (ROMP) with at least one functionality curable by ROMP,
   b) at least one initiator for initiating the ROMP curing reaction and
   c) at least one filler
   wherein the cured composition is tempered at a temperature of about 130° C. or more.

2. The composite milling block according to claim 1, wherein the cured composition is tempered at a temperature of about 160° C. or more.

3. The composite milling block according to claim 1, wherein the cured composition is tempered for about 1 h or more.

4. The composite milling block according to claim 1, wherein the composition is tempered until the compressive strength or the flexural strength or the fracture toughness or the Youngs modulus or combinations of two or more of those features are improved over the untempered material.

5. The composite milling block according to claim 1, wherein the material fulfills at least one of the following parameters:
   Flexural strength: at least about 155 MPa,
   Youngs' modulus: at least about 9200 MPa,
   L-value: more than 68,
   a-value: less than 4 and
   b-value: less than 20.5.

6. The composite milling block according to claim 1, wherein the color of the tempered material according to the L*a*b* scheme has an L-value closer to about 100 or an absolute a-value closer to about 0 or an absolute b-value closer to about 0 or a combination of two or more of these improvements, than the untempered material.

7. The composite milling block according to claim 1, wherein the at least one monomer that is curable by ring-opening metathesis polymerization (ROMP) contains at least one silicon atom.

8. The composite milling block according to claim 1, wherein the initiator contains at least one metal selected from the group consisting of Ru and Os.

9. The composite milling block according to claim 1, wherein the composition to be cured comprises
   a) about 9 to about 60% by weight of at least one monomer that is curable by ring-opening metathesis polymerization (ROMP) with at least one functionality curable by ROMP or a mixture of two or more of such monomers,
   b) about 100 to about 3000 weight ppm of at least one initiator for initiating the ROMP curing reaction, the ppm value relating to the amount of metal in the initiator in relation to the amount of monomer and
   c) about 49 to about 90% by weight of a filler or a mixture of two or more of such fillers.

10. The composite milling block according to claim 1, wherein the composition to be cured at about 50° C. shows an increase of viscosity of less than about 10% at about 50° C. for about 5 h.

11. The composite milling block according to claim 1, wherein the curing and tempering are effected in separate steps.

12. The composite milling block according to claim 1, wherein the curing and tempering are effected at equal or different temperatures.

13. The composite milling block according to claim 1, wherein tempering is effected at a temperature of about 140° C. or more.

14. The composite milling block according to claim 1, wherein the cured composition is tempered for about 30 minutes or more.

15. The composite milling block according to claim 1, wherein the cured composition is at least tempered until the flexural strength or the Youngs' modulus or a combination of those features is improved over the untempered material.

16. The composite milling block according to claim 1, wherein the cured composition is at least tempered until the color of the tempered material according to the L*a*b* scheme has an L-value closer to about 100 or an absolute a-value closer to 0 or an absolute b-value closer to 0 or a combination of two or more of these improvements, than the untempered material.

17. The composite milling block of claim 1, wherein the material is an inlay, an onlay, a veneer shell, a crown or a bridge, either permanent or temporary, artificial teeth or denture bases or denture.

18. A method for the restoration of a tooth comprising the step of milling a solid material, the solid material being part of a composite milling block as described in claim 1.

19. The method according to claim 18, wherein the solid material after milling has the shape of an inlay, onlay, veneer-shell, crown or bridge.

* * * * *

UNITED STATES PATENT AND TRADEMARK OFFICE
CERTIFICATE OF CORRECTION

PATENT NO. : 8,178,604 B2
APPLICATION NO. : 12/162429
DATED : May 15, 2012
INVENTOR(S) : Thomas Luchterhandt It is certified that error appears in the above-identified patent and that said Letters Patent is hereby corrected as shown below:

First Page, Column 2 (Other Publications)
Line 1         Delete "a a" and insert -- a --, therefor.
Line 4         Delete "Chemistr," and insert -- Chemistry, --, therefor.
Line 10        Delete "Matathesis" and insert -- Metathesis --, therefor.

Column 1
Line 20        Delete "pre-pared" and insert -- prepared --, therefor.

Column 2
Line 8         Delete "pre-pared" and insert -- prepared --, therefor.
Line 51        Delete "veneershell," and insert -- veneer shell, --, therefor.

Column 3
Line 33        Delete "tillers." and insert -- fillers. --, therefor.

Column 6
Line 34        Delete "bicylic" and insert -- bicyclic --, therefor.

Columns 13-14
Line 3 (Approx.)

Delete " 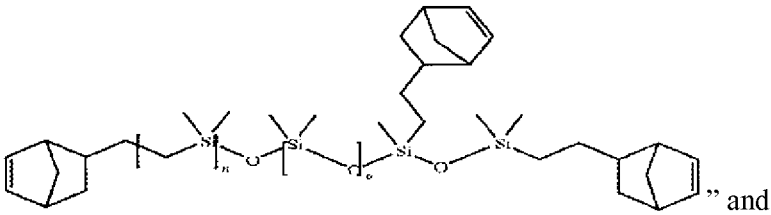 " and

Signed and Sealed this
Twenty-fifth Day of September, 2012

David J. Kappos
*Director of the United States Patent and Trademark Office*

CERTIFICATE OF CORRECTION (continued)
U.S. Pat. No. 8,178,604 B2 insert -- 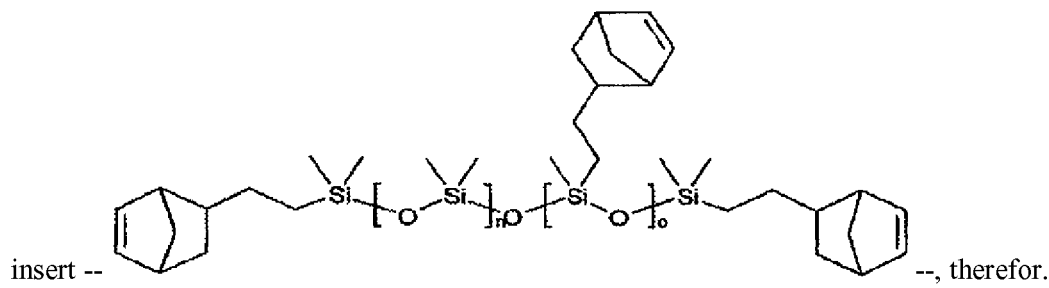 --, therefor.

Columns 13-14
Line 6 (Approx.)

Delete " 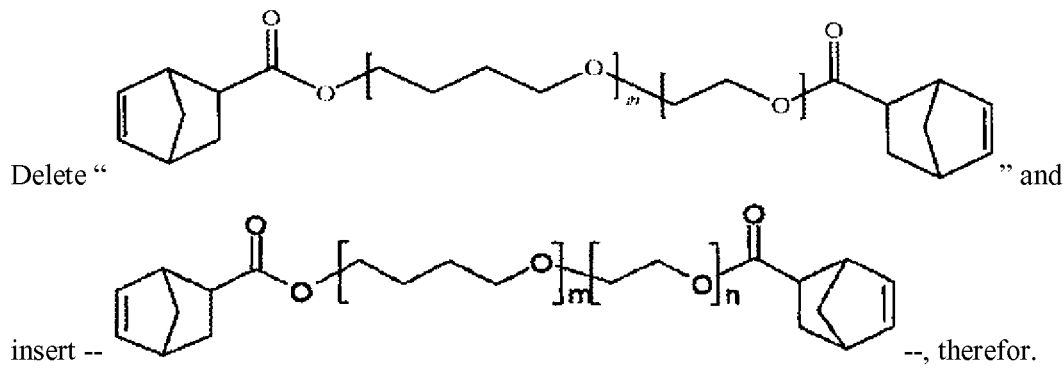 " and insert -- --, therefor.

Column 15
Line 13        Delete "Chemistr," and insert -- Chemistry, --, therefor.
Line 19        Delete "col, 10" and insert -- col. 10, --, therefor.
Line 38 (Approx.)    Delete "trifluormethansulfonate, trifluoracetate" and insert
               -- trifluoromethanesulfonate, trifluoroacetate --, therefor.
Line 42 (Approx.)    Delete "tert.-butyl" and insert -- tert-butyl --, therefor.

Column 16
Line 45        Delete "c))," and insert -- c), --, therefor.
Line 48        Delete "christobalite)" and insert -- cristobalite) --, therefor.

Column 17
Line 17        Delete "sub-stances" and insert -- substances --, therefor.
Line 28        Delete "—NR"$_{12}$" and insert -- —NR"$_2$ --, therefor.

Column 18
Line 38        Delete "tert.-butyl" and insert -- tert-butyl --, therefor.

Column 21
Line 3 (Approx.) (Compound 1)    Delete "Quarts" and insert -- Quartz --, therefor.
Line 31        Delete "Youngs's" and insert -- Young's --, therefor.

Column 24
Lines 36-37    In Claim 19, delete "veneershell," and insert -- veneer shell, --, therefor.